United States Patent
Patel et al.

(10) Patent No.: US 12,042,139 B2
(45) Date of Patent: Jul. 23, 2024

(54) KNOTLESS SUTURE ANCHORS

(71) Applicant: Medos International Sarl

(72) Inventors: Ravi Patel, Providence, RI (US);
Daniel Gamache, Dedham, MA (US);
Brian Otrando, Cumberland, RI (US);
Timothy Reppert, Foster City, CA (US); Howard C. Tang, Boston, MA (US); Joseph Hernandez, Sandwich, MA (US)

(73) Assignee: Medos International Sarl, Le Locle (CH)

( * ) Notice: Subject to any disclaimer, the term of this patent is extended or adjusted under 35 U.S.C. 154(b) by 144 days.

(21) Appl. No.: 17/241,392

(22) Filed: Apr. 27, 2021

(65) Prior Publication Data

US 2022/0338856 A1   Oct. 27, 2022

(51) Int. Cl.
*A61B 17/04* (2006.01)

(52) U.S. Cl.
CPC .... *A61B 17/0401* (2013.01); *A61B 2017/044* (2013.01); *A61B 2017/0445* (2013.01); *A61B 2017/0464* (2013.01)

(58) Field of Classification Search
CPC .............. A61B 17/0401; A61B 17/863; A61B 2017/0412; A61B 2017/0427; A61B 2017/0429; A61B 2017/043; A61B 2017/0432; A61B 2017/0433; A61B 2017/0435; A61B 2017/0437; A61B 2017/044; A61B 2017/0445;

(Continued)

(56) References Cited

U.S. PATENT DOCUMENTS 5,435,723 A * 7/1995 O'Brien ............... A61C 8/0001
   433/173
6,099,530 A   8/2000 Simonian et al.
(Continued)

FOREIGN PATENT DOCUMENTS

GB   1163619 A   9/1969

OTHER PUBLICATIONS

Extended European Search Report for Application No. EP 22170074.3, mailed on Oct. 10, 2022, 11 pages.

*Primary Examiner* — Kelly J Bekker
*Assistant Examiner* — Lindsey R. Rivers
(74) *Attorney, Agent, or Firm* — Mintz Levin Cohn Ferris Glovsky and Popeo, P.C.

(57) ABSTRACT

Systems are provided for securing tissue to bone. A suture anchor can include an elongate body having a proximal end and a distal end and an external surface with a plurality of longitudinally spaced bone-engaging features formed at least partially circumferentially thereon over at least a portion of a length of the suture anchor. The proximal end can have a lumen extending at least partially into the elongate body and the distal end can have a suture engaging feature proximate thereto. A first series of bone-engaging features can have a dimension that increases from a distal to a proximal end of each bone-engaging feature of the first series of bone-engaging features. A second series of bone-engaging features can have a dimension that decreases from a distal to a proximal end of each bone-engaging feature of the second series of bone-engaging features.

13 Claims, 9 Drawing Sheets

(58) Field of Classification Search
CPC ..... A61B 2017/0459; A61B 2017/0464; A61F 2002/0817; A61F 2002/0829
See application file for complete search history.

(56) References Cited

U.S. PATENT DOCUMENTS

| | | | | |
|---|---|---|---|---|
| 8,512,405 | B2 * | 8/2013 | Baird | A61F 2/0811 |
| | | | | 623/13.12 |
| 9,241,704 | B1 | 1/2016 | MacLeod et al. | |
| 2010/0063541 | A1 | 3/2010 | Brunelle et al. | |
| 2015/0351741 | A1 * | 12/2015 | Hawkins | A61B 17/0401 |
| | | | | 606/232 |
| 2018/0071080 | A1 | 3/2018 | Greelis | |
| 2018/0228597 | A1 | 8/2018 | McCarty, III | |
| 2019/0029666 | A1 * | 1/2019 | Bouduban | A61B 17/0401 |

* cited by examiner

KNOTLESS SUTURE ANCHORS

FIELD

The present disclosure relates generally to methods and devices for securing soft tissue to bone.

BACKGROUND

Tearing of, or complete or partial detachment of ligaments, tendons and/or other soft tissues from their associated bones within the body are commonplace injuries. Such injuries can result from excessive stresses being placed on these tissues. By way of example, tissue tearing or detachment may occur as the result of an accident such as a fall, over-exertion during a work-related activity, or during the course of an athletic event. In the case of tearing or a partial or complete detachment of soft tissue from a bone, surgery is typically required to reattach the soft tissue (or a graft tissue) to the bone.

One method of repairing such a tear is to stitch it closed by passing a length of suture through the tissue and tying the suture. Suture can also be used in conjunction with one or more suture anchors to repair such tissue tears. Sutures can be fastened to suture anchors and to tissue using knots tied by the surgeon during a repair procedure, or using "knotless" devices and methods, where one or more anchors and one or more sutures can be connected and tensioned without the surgeon needing to tie knots during the surgery. Knotless anchoring is of particular utility for minimally invasive surgeries, such as endoscopic or arthroscopic repairs, where the surgeon remotely manipulates the suture at the surgical site using tools inserted through a small percutaneous incision, small diameter cannula, or an endoscopic tube, which can make the knot-tying process difficult and tedious.

It can be challenging to maintain the desired tension on the operative suture in the course of a surgical procedure to reattach soft tissue. Further, existing suture anchors used to insert the anchors into bone may have certain disadvantages that complicate their use and/or impose certain undesirable limits.

Accordingly, there is a need for improved devices, systems, and methods for attaching tissue to bone.

SUMMARY

In one aspect, a suture anchor is provided that in some embodiments includes an elongate body having a proximal end and a distal end and an external surface with a plurality of longitudinally spaced bone-engaging features formed at least partially circumferentially thereon over at least a portion of a length of the suture anchor. The proximal end has a lumen extending at least partially into the elongate body and the distal end can have a suture engaging feature proximate thereto. A first series of bone-engaging features have a dimension that increases from a distal to a proximal end of each bone-engaging feature of the first series of bone-engaging features. A second series of bone-engaging features have a dimension that decreases from a distal to a proximal end of each bone-engaging feature of the second series of bone-engaging features.

The suture anchor can vary in numerous ways. For example, the first and second series of bone-engaging features can be spaced along a length of the external surface of the elongate body. In some embodiments, the first and second series of bone-engaging features can collectively encompass about 360° of a circumference of the elongate body. In at least some embodiments, the second series of bone-engaging features can span less than half of a circumference of the elongate body. In at least some embodiments, the second series of bone-engaging features can span about 90° to about 120° of the circumference of the elongate body.

The bone engaging feature can have various configurations. For example, each bone-engaging feature can be a wedge-like barb having a base extending radially from the external surface of the elongate body and a sloped surface extending from the base to the external surface of the elongate body. In some embodiments, the first series of bone-engaging features can have the base disposed proximal to the sloped surface and the second series of bone-engaging features can have the base disposed distal to the sloped surface. In at least some embodiments, the sloped surface can be oriented at an angle of about 15° to about 30° relative to a longitudinal axis of the elongate body. In at least some embodiments, the angle can be substantially the same for all bone-engaging surface features. In at least some embodiments, the angle can be variable based on a longitudinal position of the bone-engaging feature on the elongate body. In some embodiments, the angle can be greater at a proximal portion of the elongate body than at a distal portion of the elongate body.

The lumen can have various configurations. For example, the lumen can extend completely through the elongate body from the proximal end to the distal end. In some embodiments, the lumen can be offset from a longitudinal axis of the elongate body.

The suture engaging feature can have various configurations. For example, the suture engaging feature can include an aperture notch in proximity to the distal end. In some embodiments, the suture engaging feature can include a pair of longitudinally positioned arms forming a channel arranged proximal to the distal end.

In another aspect, a suture anchor is provided that in some embodiments includes an elongate body having a proximal end and a distal end and an external surface with a plurality of longitudinally spaced bone-engaging features formed at least partially circumferentially thereon over at least a portion of a length of the elongate body. The proximal end has a lumen extending at least partially into the elongate body and the distal end has a suture engaging feature proximate thereto. Each bone-engaging feature is a wedge-like barb having a base extending radially from the external surface of the elongate body and a sloped surface extending from the base to the external surface of the elongate body. The sloped surface is oriented at an angle that is variable based on the longitudinal position of the bone-engaging feature on the elongate body.

The suture anchor can have various configurations. For example, the angle can be greater at a proximal portion of the elongate body than at a distal portion of the elongate body. In some embodiments, the angle can increase at a fixed interval from a distal-most arranged bone-engaging feature to a proximal-most arranged bone-engaging feature. In at least some embodiments, the sloped surface can be oriented at an angle relative to a longitudinal axis of the elongate body that ranges from about 15° proximate the distal end of the elongate body to about 30° proximate to the proximal end of the elongate body. In at least some embodiments, the angle can increase gradually along the length of the elongate body or the angle increases in a step-wise manner based upon longitudinally spaced regions of the elongate body.

BRIEF DESCRIPTION OF THE DRAWINGS

The present disclosure will be more fully understood from the following detailed description taken in conjunction with the accompanying drawings, in which.

DETAILED DESCRIPTION

Figure 1:
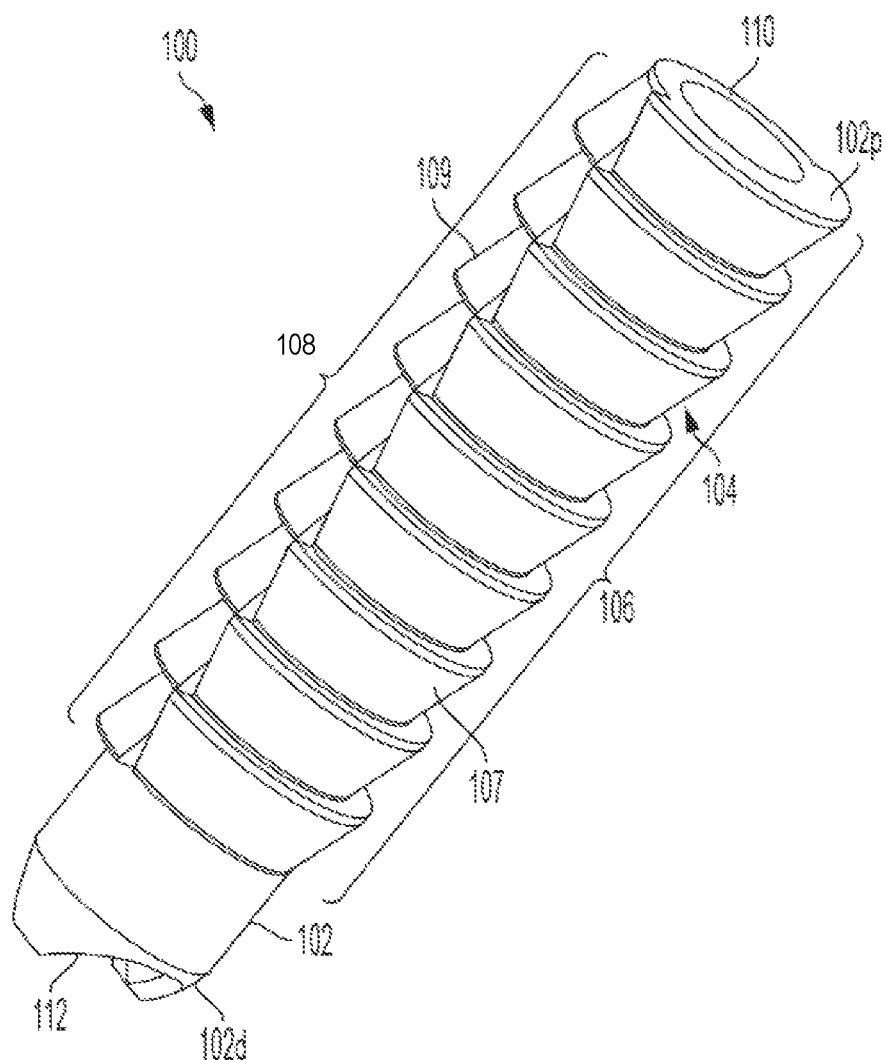
FIG. 1 is a perspective view of one embodiment of a suture anchor.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used. In addition, the terms "about" and "substantially" are defined as ranges based on manufacturing variations and variations over temperature and other parameters.

Successful soft tissue repair surgery, such as rotator cuff repair, requires that the suture anchor be securely engaged within bone to avoid migration and/or dislodgement, and that the operative suture attached to the soft tissue and maintained against the bone by the suture anchor resist migration when subjected to loads. The most common mode of failure is due to suture migration or slippage, which occurs when the load applied to the operative suture exceeds the force applied by the suture anchor to compress the operative suture against the bone in which the suture anchor is implanted. Suture migration occurs at lower loads than does suture anchor migration or dislodgement. The suture anchors described herein provide anchor designs optimized to maintain sufficient force on the operative suture to avoid suture migration, while maintaining secure engagement of the anchor within bone.

In at least some of the described embodiments, a suture anchor is provided that includes variable bone-engaging features that enable the anchor to be maintained within bone with sufficient integrity while enabling the anchor to provide selectively increased force on the operative suture to enable it to resist suture migration to a greater extent. During the course of a surgical procedure utilizing the suture anchors described herein, which is typically conducted arthroscopically, the suture anchor is removably disposed on an elongate shaft of an inserter device to deliver the suture anchor to its implantation site.

In one embodiment described and illustrated herein, the variable bone-engaging features of the suture anchor can be reverse angle barbs arranged along the length of a portion of the suture anchor. In another embodiment, variable angle bone-engaging features of the suture anchor can be barbs in which an angle of the barb is a variable angle based on the barb's axial location along the suture anchor. In the embodiment including the reverse angle barbs, the operative suture used to secure soft tissue to bone interacts with the reverse barbs on a portion of the anchor, such as the side of the anchor in proximity to the soft tissue to be reattached, to selectively increase the force exerted on the operative suture to maintain a desired level of tension with a reduced incidence of suture migration. In this way, when the suture anchor is driven into a bone (e.g., by using the inserter tool or other suitable instrument), the reverse angle barbs keep the operative suture tensioned, while the combination of the reverse angle barbs and the traditional angle barbs cooperate to maintain the suture anchor securely seated within the bone hole.

Similarly, in the embodiment including the variable angle barbs, the operative suture used to secure soft tissue to bone interacts with the variable barbs in order to selectively increase the force applied to the operative suture at different positions on the anchor (e.g., different axial and/or radial positions) to maintain a desired level of tension with a reduced incidence of suture migration. The variable angle barbs can be designed such that in at least a portion of the anchor the proximal barbs can have a greater angle than more distally disposed barbs. As will be described below, the barb angle can vary such that the angle of the barb increases gradually in the distal to proximal direction. Alternatively, the barbs can have the same angle in certain regions along the axial length of the anchor and the barb angle of each region increases in the distal to proximal direction along the length of the anchor. In this way the distal barbs allow for easier insertion of the anchor into a bone hole while the proximally positioned barbs applying a greater suture retention force to the operative suture, enabling the operative suture to resist migration.

Figure 2:
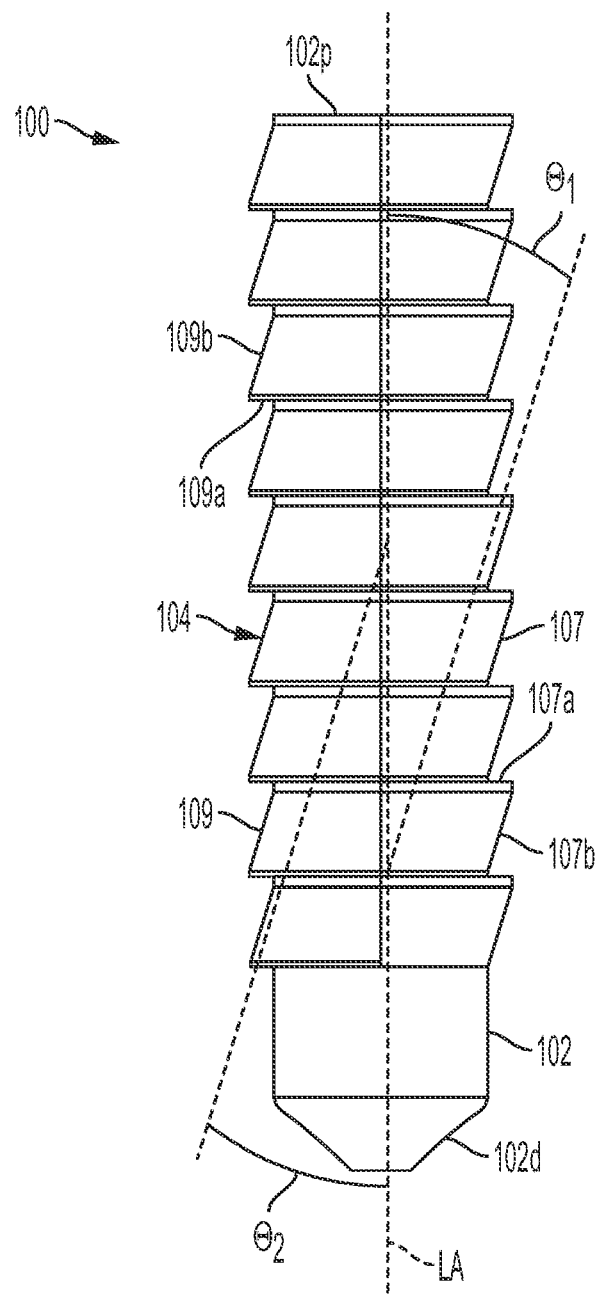
FIG. 2 is a side view of the suture anchor of FIG. 1.

FIGS. 1-2 illustrate one embodiment of a suture anchor 100 that includes an elongate body 102 having a proximal end 102*p*, a distal end 102*d*, and an external surface 104 with a first series of bone-engaging features 106 and a second series of bone-engaging features 108. In this embodiment, each of the plurality of longitudinally spaced bone-engaging features 106, 108 can be formed at least partially circumferentially on the external surface 104 over at least a portion of a length of the suture anchor 100. The proximal end 102*p* can have a lumen 110 extending at least partially into the elongate body 102, with the lumen 110 being configured to removably secure the anchor 100 to an inserter shaft, as described in detail below. Although the lumen illustrated in FIGS. 1-2 terminates within the anchor body 102, a person skilled in the art will understand that the lumen 110 can extend entirely through the anchor body 102 from the proximal end 102p to the distal end. Although the illustrated lumen 110 is shown to be aligned with a longitudinal axis LA of the elongate body 102, the lumen 110 can alternatively be offset from the longitudinal axis LA.

The distal end 102d of the anchor 100 can have a suture engaging feature 112 that enables an operative suture to be engaged by the anchor 100 as the anchor 100 is implanted in bone during a surgical procedure to reattach soft tissue to bone. While the suture engaging feature 112 can take a variety of forms that will be understood by a person skilled in the art, in the embodiment illustrated in FIGS. 1-2, the suture engaging feature 112 is a notch that is disposed in proximity to the distal end 102d. Alternative designs for the suture engaging feature 112 can include but are not limited to an aperture, a groove, etc.

The first and second series of bone-engaging features 106, 108 can be disposed over at least a portion of, and generally a majority of, a length of the external surface 104 of the elongate body 102. Additionally, the first and second series of bone-engaging features 106, 108 can collectively encompass about 360° of a circumference of the elongate body 102. In one embodiment, the second series of bone-engaging features 108 can span less than half of a circumference of the elongate body 102, such as in a range of about 90° to about 120° of the circumference of the elongate body 102.

The first and second series of bone-engaging features 106, 108 can have various configurations. For example, the first series and second series of bone-engaging features 106, 108 are formed from individual bone-engaging features 107, 109. In this embodiment, each of the bone-engaging features 107, 109 is a wedge-like barb including a base 107a, 109a extending radially from the external surface 104 of the elongate body 102, and a sloped surface 107b, 109b extending away from the base 107a, 109a back to the external surface 104 of the elongate body 102. Each of the first series of bone-engaging features 107 can have the base 107a disposed proximal to the sloped surface 107b, while each of the second series of bone-engaging features 109 can have the base 109a disposed distal to the sloped surface 109b. In other words, the barbs 107 of the first series of bone-engaging features 106 have a barb width that increases in the direction of distal to proximal (i.e., in the direction of anchor insertion), allowing for generally easier insertion of the anchor into a bone hole sized for an interference fit with the anchor. Conversely, the barbs 109 of the second series of bone-engaging features 108 have a barb width that decreases in the direction of distal to proximal. Accordingly, the barbs 109 are sometimes referred to herein as "reverse angle" barbs or as having a "reverse angle." It is understood that when the bone-engaging features are wedge-like barbs, the interface between the base 107a and the sloped surface 107b can be, but need not be, a sharp corner. Rather, this interface can be somewhat rounded or generally parallel to longitudinal axis LA.

Although the presence of the reverse angle barbs 109 can cause additional resistance to insertion of the anchor 100 within a bone hole, reverse angle barbs 109 tend to exert more force on the operative suture, thus reducing the chance of suture migration.

Each bone-engaging feature 107 of the first series of bone-engaging features 106 can have a dimension, such as the slope angle $\Theta_1$ of the sloped surface 107b, which increases from a distal to a proximal end of each bone-engaging feature 107 of the first series of bone-engaging features 106. Similarly, each bone-engaging feature 109 of the second series of bone-engaging features 108 can have a dimension, such as the slope angle $\Theta_2$ of the sloped surface 109b, which decreases from a distal to a proximal end of each bone-engaging feature 109 of the second series of bone-engaging features 108. In this embodiment, the sloped surfaces 107b, 109b can be oriented such that the slope angles $\Theta_1$, $\Theta_2$ are within the range of about 15° to about 30° relative to a longitudinal axis LA of the elongate body 102. The slope angle $\Theta_1$, for all bone-engaging features 107 of the first series of bone engaging features 106 can be substantially the same as slope angle $\Theta_2$ for all bone-engaging features 109 of the second series of bone engaging features 108, or the slope angles $\Theta_1$, $\Theta_2$ can vary within each of the first and second series of bone engaging features 106, 108.

Figure 3:
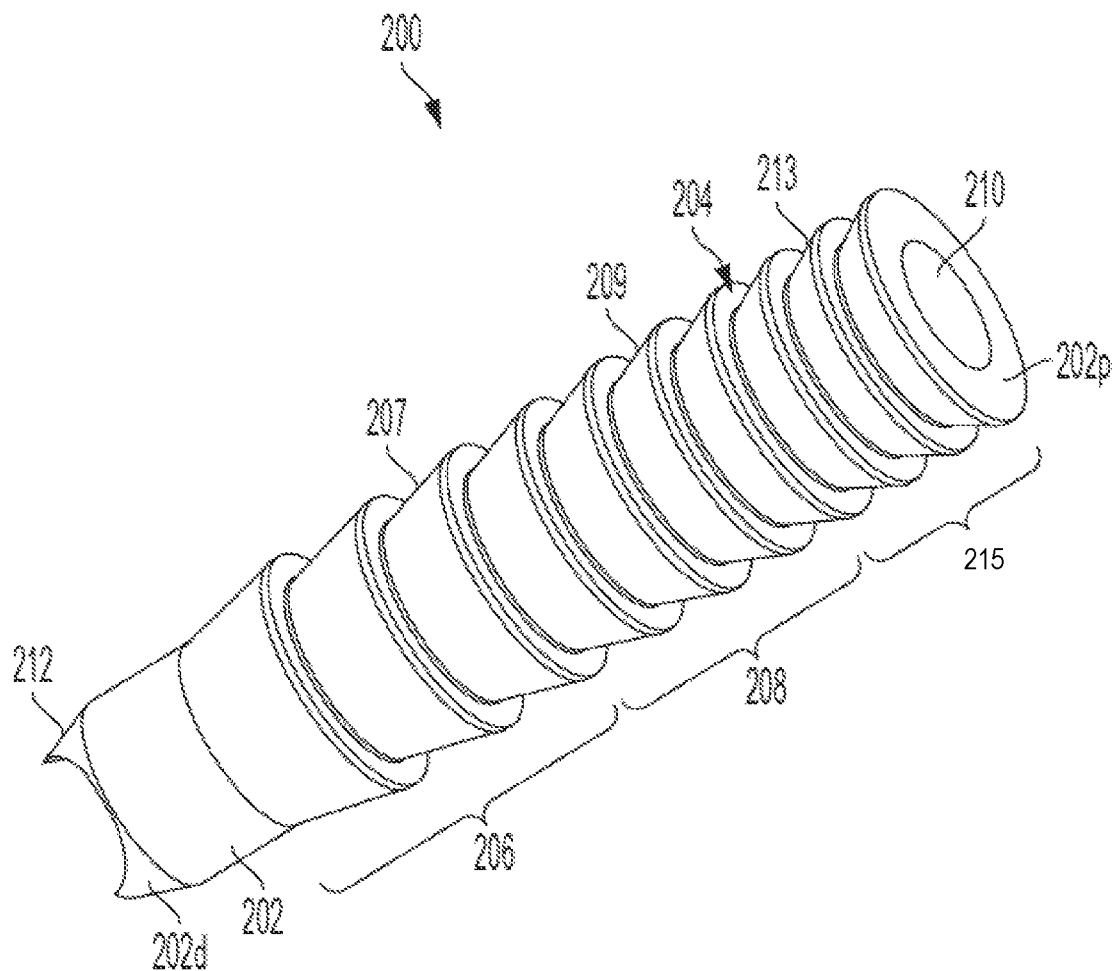
FIG. 3 is a perspective view of another embodiment of a suture anchor.
Figure 4:
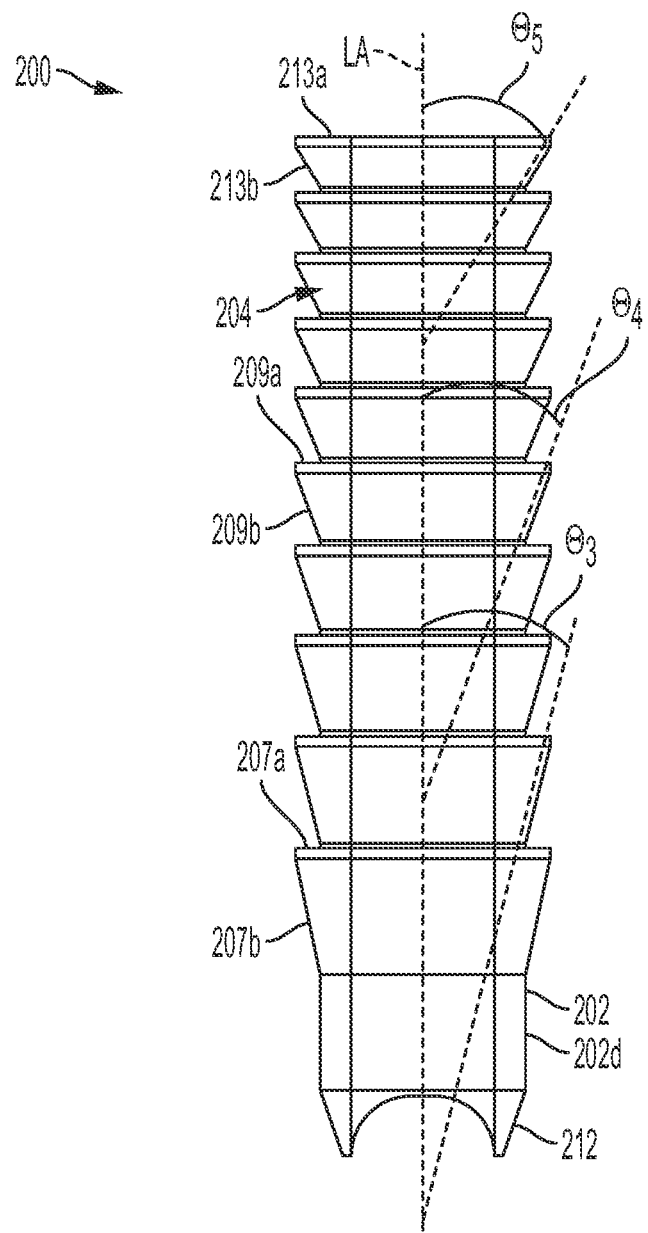
FIG. 4 is a side view of the suture anchor of FIG. 3.
Figure 5:
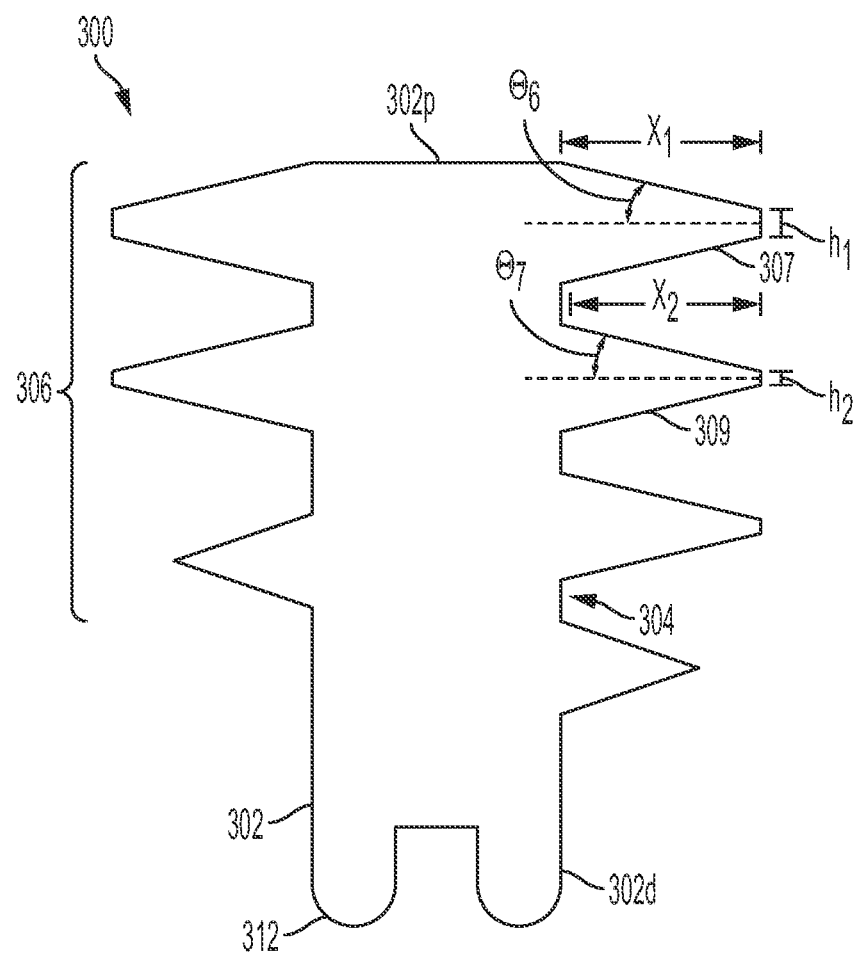
FIG. 5 is a side view of another embodiment of a suture anchor.
Figure 6:
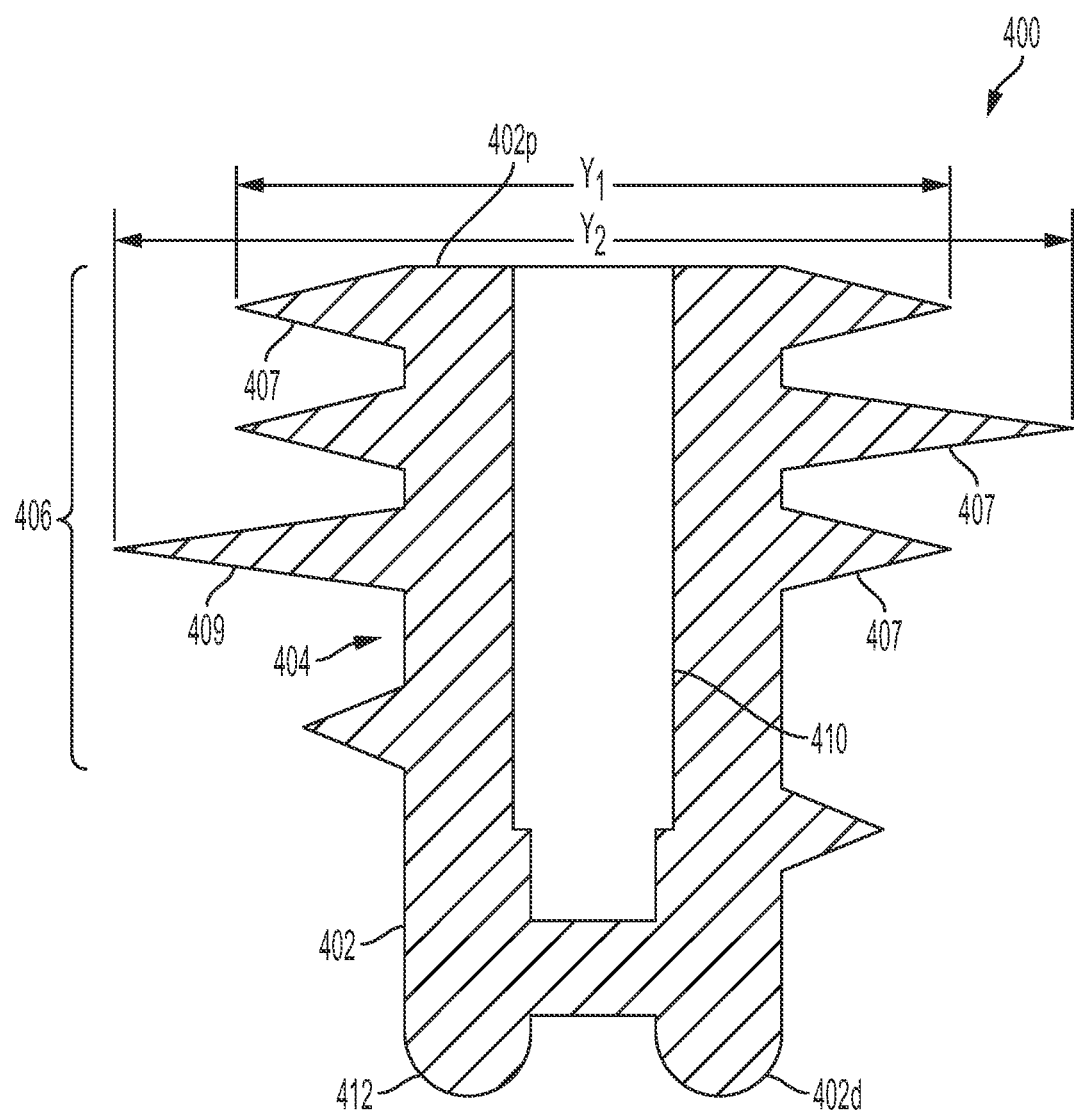
FIG. 6 is a side view of another embodiment of a suture anchor.

As indicated above, the suture anchor can include various types of bone-engaging features. By way of non-limiting example, FIGS. 3-4 illustrate another embodiment of a suture anchor 200 that includes a series of bone engaging features 206 having variable angled barbs. FIG. 5 illustrates a further embodiment of a suture anchor 300 that includes a series of variable threaded bone-engaging features 306. FIG. 6 illustrates yet another embodiment of a suture anchor 400 that includes a series of variable threaded bone-engaging features 406.

Similar to the suture anchor 100, FIGS. 3-4 illustrate an embodiment of a suture anchor 200 that includes an elongate body 202 having a proximal end 202p, a distal end 202d, and an external surface 204 with various grouping of bone-engaging features in which the bone-engaging features within each grouping are oriented at a different angle. By way of example, FIGS. 3-4 illustrate an embodiment that has a first series of bone-engaging features 206, a second series of bone-engaging features 208, and a third series of bone engaging features 215. In this embodiment, the each of the plurality of longitudinally spaced bone-engaging features 206, 208, 215 can be formed at least partially circumferentially on the external surface 204 over at least a portion of a length of the suture anchor 200. The proximal end 202p can have a lumen 210 extending at least partially into the elongate body 202, with the lumen 210 being configured to removably secure the anchor 200 to an inserter shaft, as described in detail below. Although the lumen illustrated in FIGS. 3-4 terminates within the anchor body 202, a person skilled in the art will understand that the lumen 210 can extend entirely through the anchor body 202 from the proximal end 202p to the distal end. Although the illustrated lumen 210 is shown to be aligned with a longitudinal axis LA of the elongate body 202, the lumen 210 can alternatively be offset from the longitudinal axis LA.

Similar to the anchor 100, the distal end 202d of the anchor 200 can have a suture engaging feature 212 arranged on the distal end 202d that enables an operative suture to be engaged by the anchor 200 as the anchor 200 is implanted in bone during a surgical procedure to reattach soft tissue to bone. While the suture engaging feature 212 can take a variety of forms that will be understood by a person skilled in the art, in the embodiment illustrated in FIGS. 3-4, the suture engaging feature 212 is a notch that is disposed in proximity to the distal end 202d. Alternative designs for the suture engaging feature 212 can include but are not limited to an aperture, a groove, etc.

The first, second, and third series of bone-engaging features 206, 208, 212 can be disposed over at least a portion of, and generally a majority of, a length of the external surface 204 of the elongate body 202. In one embodiment, the first, second, and third series of bone-engaging features 206, 208, 212 can each span about a third of the length of a total length of the elongate body 202. A person skilled in the art will appreciate that each series of bone-engaging features, which can be greater or less than three in number, can span different or variable amounts of a total length of the elongate body 202. Additionally, the first, second, and third series of bone-engaging features 206, 208, 212 can each encompass about 360° of a circumference of the elongate body 202.

The first, second, and third series of bone-engaging features 206, 208, 212 can have various configurations. For example, the first, second, and third series of bone-engaging features 206, 208, 212 are formed from individual bone-engaging features 207, 209, 213. In this embodiment, each of the individual bone-engaging features 207, 209, 213 is a wedge-like barb including a base 207a, 209a, 213a extending radially from the external surface 204 of the elongate body 202, and a sloped surface 207b, 209b, 213b extending away from the base 207a, 209a, 213a back to the external surface 204 of the elongate body 202. Each of the first series of bone-engaging features 207 can have the base 207a disposed proximal to the sloped surface 207b, each of the second series of bone-engaging features 209 can have the base 209a disposed proximal to the sloped surface 209b, and each of the third series of bone-engaging features 213 can have the base 213a disposed proximal to the sloped surface 213b.

Each bone-engaging feature 207 of the first series of bone-engaging features 206 can have a dimension, such as the slope angle $\Theta_3$ of the sloped surface 207b, which can be identical for each bone-engaging feature 207 within the first series of bone-engaging features 206, or can increase with each successive bone-engaging feature 207 within the first series of bone-engaging features 206 from a distal to a proximal end of the first series of bone-engaging features 206. Additionally, each bone-engaging feature 209 of the second series of bone-engaging features 208 can have a dimension, such as the slope angle $\Theta_4$ of the sloped surface 209b, which can be identical for each bone-engaging feature 209 within the second series of bone-engaging features 208, or can increase with each successive bone-engaging feature 209 within the second series of bone-engaging features 208 from a distal to a proximal end of the second series of bone-engaging features 208. Also, each bone-engaging feature 213 of the third series of bone-engaging features 212 can have a dimension, such as the slope angle $\Theta_5$ of the sloped surface 213b, which can be identical for each bone-engaging feature 213 within the third series of bone-engaging features 212, or can increase with each successive bone-engaging feature 213 within the third series of bone-engaging features 212 from a distal to a proximal end of the third series of bone-engaging features 212.

In this embodiment, the sloped surfaces 207b, 209b, 213b can be oriented such that the slope angles $\Theta_3$, $\Theta_4$, $\Theta_5$ are within the range of about 15° to about 30° relative to a longitudinal axis LA of the elongate body 202. Additionally, in this embodiment, each slope angle of each bone-engaging feature can be variable based on the longitudinal position of the bone-engaging feature on the elongate body 202. The slope angles for the bone-engaging features are greater at the proximal portion 202p of the elongate body 202 than at the distal portion 202d of the elongate body 202. For example, the slope angle $\Theta_3$ is less than the slope angle $\Theta_4$, and the slope angle $\Theta_4$ is less than the slope angle $\Theta_5$. The variation in the slope angles can have a variety of configurations when moving from the distal end 202d to the proximal end 202p.

For example, the slope angles of each successive bone-engaging feature can increase at a fixed interval from a distal-most arranged bone-engaging feature 207 to a proximal-most arranged bone-engaging feature 209. Additionally, another configuration can include the slope angle of each successive bone-engaging feature increasing gradually along the length of the elongate body 202, or the slope angle increases in a step-wise manner based upon longitudinally spaced regions of the elongate body 202. In this embodiment, the larger the slope angle is, the greater the force to which the operative sutures are exposed, thus minimizing the risk of suture migration after implantation of the suture anchor 200.

In other words, the barbs 207 of the first series of bone-engaging features 206 have a slope angle $\Theta_3$ allowing for generally easier insertion of the anchor into a bone hole sized for an interference fit with the anchor. Conversely, the barbs 213 of the third series of bone-engaging features 212 have a slope angle $\Theta_5$ allowing for generally more force to be exerted on the operative suture, thus reducing the chance of suture migration.

As stated above, FIG. 5 illustrates one embodiment of a suture anchor 300 that includes an elongate body 302 having a proximal end 302p, a distal end 302d, and an external surface 304 with a series of bone-engaging features 306. In this embodiment, the series of plurality of longitudinally spaced bone-engaging features 306 can be formed at least partially circumferentially on the external surface 304 over at least a portion of a length of the suture anchor 300. The proximal end 302p can have a lumen (not shown) extending at least partially into the elongate body 302, with the lumen being configured to removably secure the anchor 300 to an inserter shaft, as described in detail below. Although the lumen terminates within the anchor body 302, a person skilled in the art will understand that the lumen can extend entirely through the anchor body 302 from the proximal end 302p to the distal end 302d.

Similar to the suture anchor 100, the distal end 302d of the anchor 300 can have a suture engaging feature 312 arranged on the distal end 302d that enables an operative suture to be engaged by the anchor 300 as the anchor 300 is implanted in bone during a surgical procedure to reattach soft tissue to bone. While the suture engaging feature 312 can take a variety of forms that will be understood by a person skilled in the art, in the embodiment illustrated in FIG. 5, the suture engaging feature 312 is a notch that is disposed in proximity to the distal end 302d. Alternative designs for the suture engaging feature 312 can include but are not limited to an aperture, a groove, etc.

The series of bone-engaging features 306 can be disposed over at least a portion of, and generally a majority of, a length of the external surface 304 of the elongate body 302. In one embodiment, the series of bone-engaging features 306 can encompass about 360° of a circumference of the elongate body 302. The series of bone-engaging features 306 can have various configurations. For example, the series of bone-engaging features 306 is formed from individual bone-engaging features 307, 309. In this embodiment, each of the individual bone-engaging features 307, 309 is a thread with a varying thread form extending radially from the external surface 304 of the elongate body 302.

In this embodiment, the length $x_1$, height $h_1$, and slope angle $\Theta_6$ of the bone-engaging features 307 can be smaller than the length $x_2$, height $h_2$, and slope angle $\Theta_7$ of the bone-engaging features 309. The variation in the length, height, and slope angle can have a variety of configurations when moving from the distal end 302d to the proximal end 302p. For example, the length, height, and slope angles of each successive bone-engaging feature can increase at a fixed interval from a distally arranged bone-engaging feature 309 to a proximally arranged bone-engaging feature 307. The length, height, and slope angle of each successive bone-engaging feature can increase at a fixed interval from a distal-most arranged bone-engaging feature to a proximal-most arranged bone-engaging feature. In this embodiment, the larger the length, height, and slope angle allows for generally more force to be exerted on the operative suture, thus reducing the chance of suture migration. Additionally, the smaller the length, height, and slope angles allows for generally easier insertion of the anchor into a bone hole sized for an interference fit with the anchor.

Additionally, FIG. 6 illustrates one embodiment of a suture anchor 400 that includes an elongate body 402 having a proximal end 402p, a distal end 402d, and an external surface 404 with a series of bone-engaging features 406. In this embodiment, the series of plurality of longitudinally spaced bone-engaging features 406 can be formed at least partially circumferentially on the external surface 404 over at least a portion of a length of the suture anchor 400. The proximal end 402p can have a lumen 410 extending at least partially into the elongate body 402, with the lumen 410 being configured to removably secure the anchor 400 to an inserter shaft, as described in detail below. Although the lumen 410 terminates within the anchor body 402, a person skilled in the art will understand that the lumen can extend entirely through the anchor body 402 from the proximal end 402b to the distal end 402d.

Similar to the suture anchor 300, the distal end 402d of the anchor 400 can have a suture engaging feature 412 arranged on the distal end 402d that enables an operative suture to be engaged by the anchor 400 as the anchor 400 is implanted in bone during a surgical procedure to reattach soft tissue to bone. While the suture engaging feature 412 can take a variety of forms that will be understood by a person skilled in the art, in the embodiment illustrated in FIG. 6, the suture engaging feature 412 is a notch that is disposed in proximity to the distal end 402d. Alternative designs for the suture engaging feature 412 can include but are not limited to an aperture, a groove, etc.

The series of bone-engaging features 406 can be disposed over at least a portion of, and generally a majority of, a length of the external surface 404 of the elongate body 402. In one embodiment, the series of bone-engaging features 406 can encompass about 360° of a circumference of the elongate body 402. The series of bone-engaging features 406 can have various configurations. For example, the series of bone-engaging features 406 is formed from individual bone-engaging features 407, 409. In this embodiment, each of the individual bone-engaging features 407, 409 is a thread with an alternative varying thread form extending radially from the external surface 404 of the elongate body 402, similar to the previous embodiments of the suture anchors.

In this embodiment, the threads 407 can be identical, having a length $Y_1$, and can be arranged along the length of the elongate body 402. The thread 409 can be a thread which has a larger length $Y_2$ that the threads 407, and is arranged between two threads 407. In this embodiment, the larger the length of a thread allows for generally more force to be exerted on the operative suture, thus reducing the chance of suture migration and providing generally greater fixation in bone. Additionally, the smaller the length of a thread allows for generally easier insertion of the anchor into a bone hole sized for an interference fit with the anchor.

As indicated above, the suture anchor can include various types of bone-engaging features. By way of non-limiting example, FIG. 7 illustrates another embodiment of a suture anchor 650 that includes a series of bone engaging features 506, 508, 512 in the form of variable diameter barbs.

Figure 7:
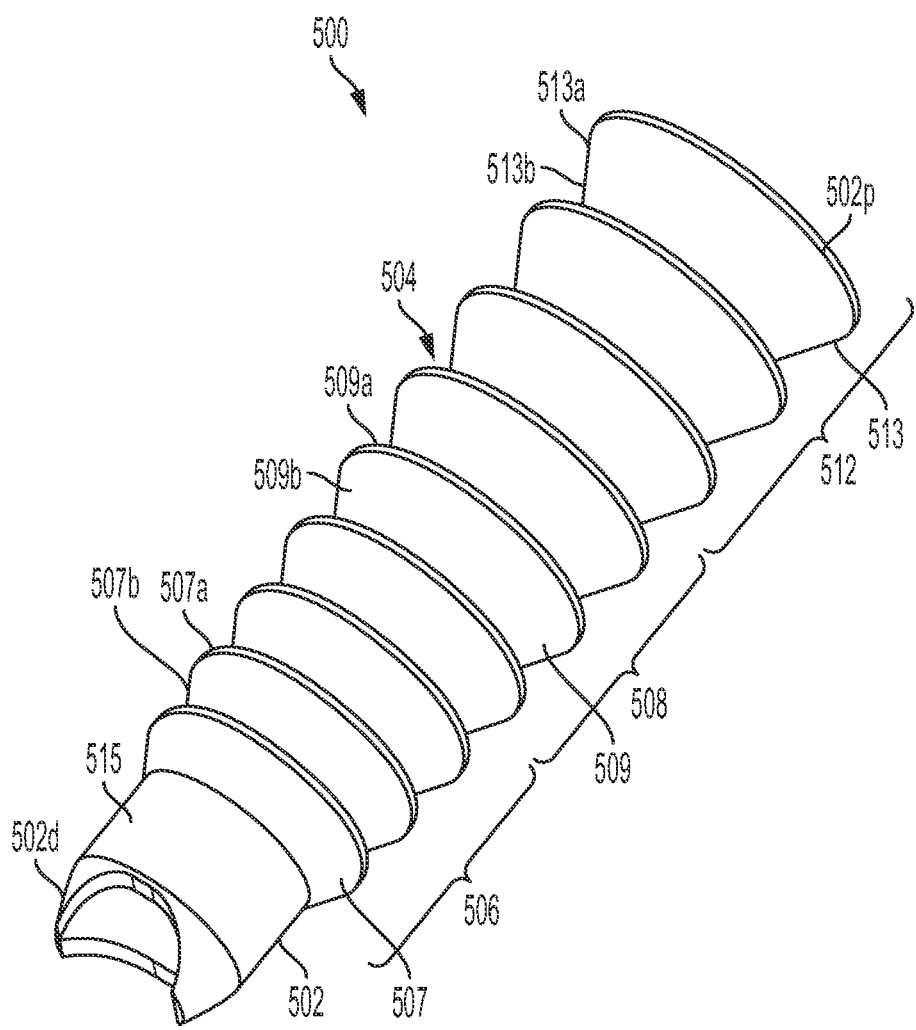
FIG. 7 is a side view of another embodiment of a suture anchor.

Similar to the suture anchor 100, FIG. 7 illustrates an embodiment of a suture anchor 500 that includes an elongate body 502 having a proximal end 502p, a distal end 502d, and an external surface 504 with various groupings of bone-engaging features in which the bone-engaging features within each grouping have a different diameter. By way of example, FIG. 7 illustrates an embodiment that has a first series of bone-engaging features 506, a second series of bone-engaging features 508, and a third series of bone engaging features 512. In this embodiment, the each of the plurality of longitudinally spaced bone-engaging features 506, 508, 512 can be formed at least partially circumferentially on the external surface 504 over at least a portion of a length of the suture anchor 500. The proximal end 502p can have a lumen extending at least partially into the elongate body 502, with the lumen being configured to removably secure the anchor 500 to an inserter shaft, as described below.

Similar to the anchor 100, the distal end 502d of the anchor 500 can have a suture engaging feature 515 arranged on the distal end 502d that enables an operative suture to be engaged by the anchor 500 as the anchor 500 is implanted in bone during a surgical procedure to reattach soft tissue to bone. The first, second, and third series of bone-engaging features 506, 508, 512 can be disposed over at least a portion of, and generally a majority of, a length of the external surface 504 of the elongate body 502. In one embodiment, the first, second, and third series of bone-engaging features 506, 508, 512 can each span about a third of the length of a total length of the elongate body 502. A person skilled in the art will appreciate that each series of bone-engaging features, which can be greater or less than three in number, can span different or variable amounts of a total length of the elongate body 502. Additionally, the first, second, and third series of bone-engaging features 506, 508, 512 can each encompass about 360° of a circumference of the elongate body 502.

The first, second, and third series of bone-engaging features 506, 508, 512 can have various configurations. For example, the first, second, and third series of bone-engaging features 506, 508, 512 are formed from individual bone-engaging features 507, 509, 513. In this embodiment, each of the individual bone-engaging features 507, 509, 513 is a wedge-like barb including a base 507a, 509a, 513a extending radially from the external surface 504 of the elongate body 502, and a sloped surface 507b, 509b, 513b extending away from the base 507a, 509a, 513a back to the external surface 504 of the elongate body 502.

Each bone-engaging feature 507 of the first series of bone-engaging features 506 can have a dimension, such as the diameter of the base 507a, which can be identical for each bone-engaging feature 507 within the first series of bone-engaging features 506, or can increase with each successive bone-engaging feature 507 within the first series of bone-engaging features 506 from a distal to a proximal end of the first series of bone-engaging features 506. Additionally, each bone-engaging feature 509 of the second series of bone-engaging features 508 can have a dimension, such as the diameter of the base 509a, which can be identical for each bone-engaging feature 509 within the second series of bone-engaging features 508, or can increase with each successive bone-engaging feature 509 within the second series of bone-engaging features 508 from a distal to a proximal end of the second series of bone-engaging features 508. Also, each bone-engaging feature 513 of the third series of bone-engaging features 512 can have a dimension, such as the diameter of the base 513a, which can be identical for each bone-engaging feature 513 within the third series of bone-engaging features 512, or can increase with each successive bone-engaging feature 513 within the third series of bone-engaging features 512 from a distal to a proximal end of the third series of bone-engaging features 512.

In this embodiment, each diameter of each bone-engaging feature can be variable based on the longitudinal position of the bone-engaging feature on the elongate body 502. The diameter for the bone-engaging features are greater at the proximal portion 502p of the elongate body 602 than at the distal portion 502d of the elongate body 502. The variation in the diameter can have a variety of configurations when moving from the distal end 502d to the proximal end 502p. For example, the diameter of each successive bone-engaging feature can increase at a fixed interval from a distal-most arranged bone-engaging feature 507 to a proximal-most arranged bone-engaging feature 509. Additionally, another configuration can include the diameter of each successive bone-engaging feature increasing gradually along the length of the elongate body 502, or the diameter increases in a step-wise manner based upon longitudinally spaced regions of the elongate body 502. In this embodiment, the larger the diameter is, the greater the force to which the operative sutures are exposed, thus minimizing the risk of suture migration after implantation of the suture anchor 500.

Figure 8:
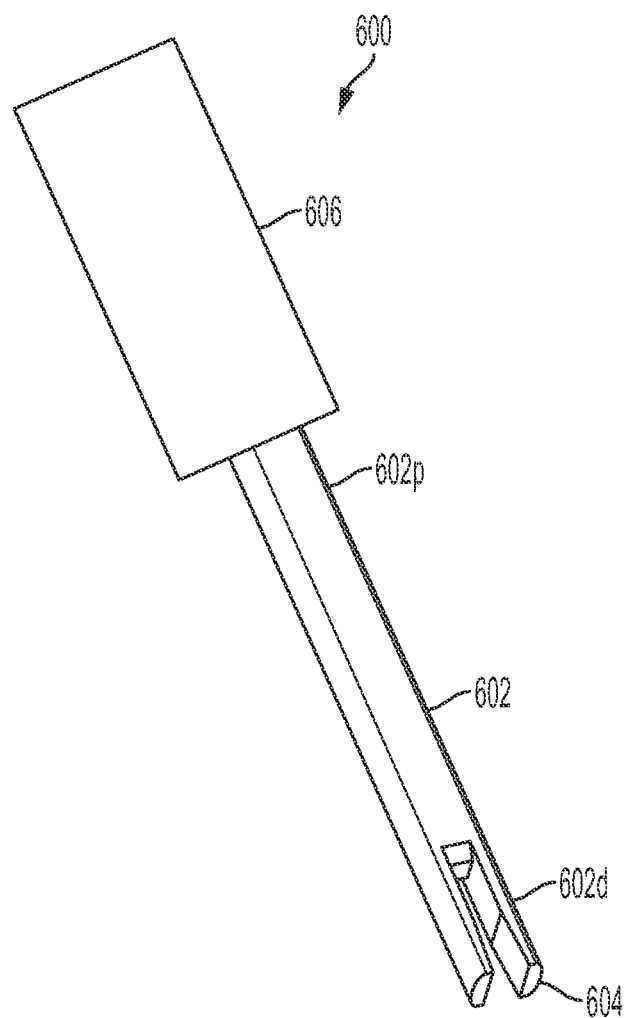
FIG. 8 is a perspective view of one embodiment of an inserter device useful in a surgical procedure to reattach soft tissue using a suture anchor of the type described herein.

In order to insert the suture anchor 100 into bone, an inserter tool can be used to help align and push the suture anchor into bone. As illustrated in FIG. 8, an inserter tool 600 can be of a type known to a person skilled in that art and it includes an elongate body 602, one or more engagement features 604 arranged at the distal end 602d of the elongate body 602, and a handle 606 arranged at the proximal end 602p of the elongate body 602. The engagement features 604 can be configured to engage with a suture anchor 100. It should be appreciated that the engagement features 604 can have various configurations. For example, in the illustrated embodiment, the engagement features 604 are a fork including a notch to engage with complementary features within the lumen 110 of an anchor 100.

A person skilled in the art will appreciate that the suture anchors described herein can be used in a variety of surgical techniques to secure and/or reattach soft tissue to bone. The surgical procedure can be conducted as an open surgical procedure or as a minimally invasive surgical procedure such as an arthroscopic procedure. Following preparation of the patient, an appropriate incision is made to access the surgical site. One or more holes are formed in bone, in proximity to the tissue repair site, to receive the one or more anchors to be used to anchor the soft tissue. One or more strands of operative suture are then passed through the detached tissue and then coupled to or positioned adjacent to the one or more suture anchors to be used in the procedure. The one or more suture anchors are then implanted into the corresponding bone hole(s) using an appropriate inserter tool and the operative sutures are appropriately tensioned, before or after insertion of the anchor, to bring the detached tissue in proximity to bone. In so doing, the operative suture(s) are compressed within the bone hole between the anchor and the wall that defines the bone hole. Once the anchor is properly seated and the tissue is properly positioned adjacent to bone, the suture is tied off (either by cinching or tying a knot), any excess suture is removed, and the incision is closed.

Figure 9:
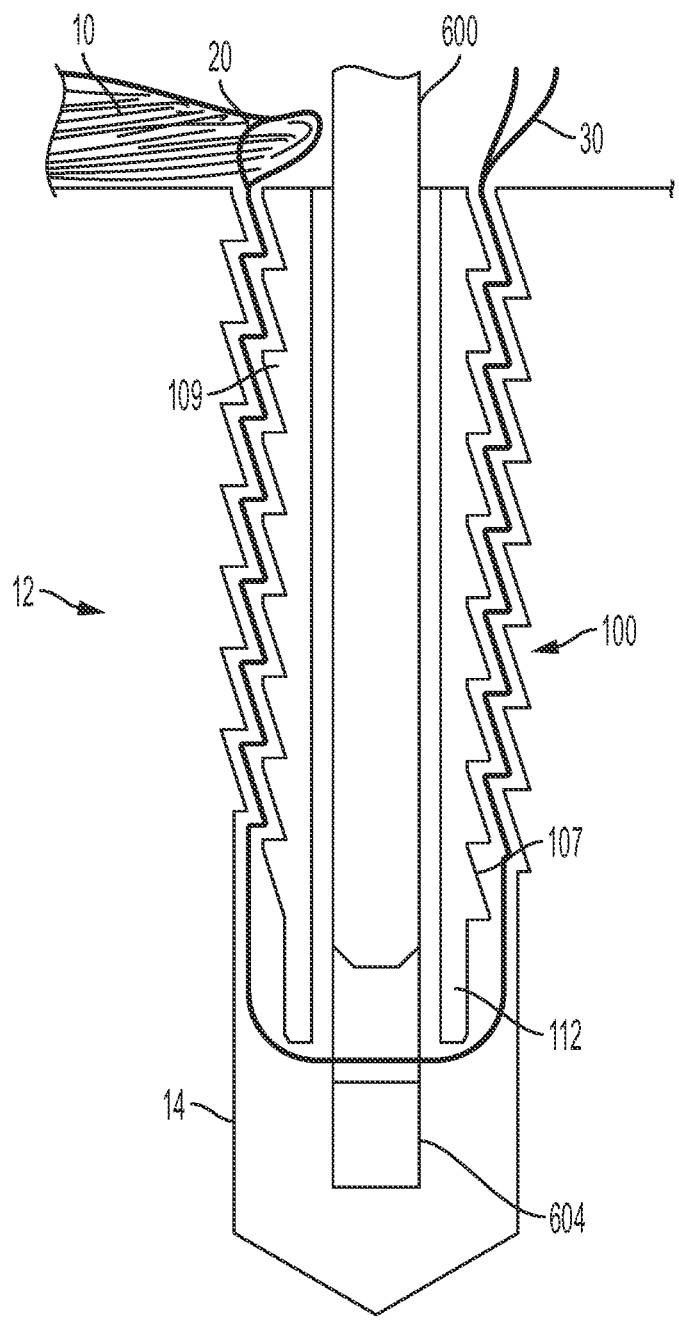
FIG. 9 schematically illustrates a method using a surgical system including the suture anchor of FIG. 1 to reattach soft tissue to bone.

FIG. 9 illustrates the final stages of such a procedure in which the suture anchor 100 secures soft tissue 10 to bone 12. The suture anchor 100 is mounted on the distal end 602d of the inserter tool 600 (which has yet to be removed) with the distal end 602d removably secured within the lumen 110 of the suture anchor 100. As shown, the operative suture 20, having free ends 30, is secured to the soft tissue 10 and then fed through the suture engaging feature 112 of suture anchor 100. With the operative suture 20 connected to the anchor 100, the suture anchor 100 is disposed in a previously drilled bone hole 14. Once the suture anchor 100 is properly seated, the inserter tool 600 is removed leaving the suture anchor 100 within the bone hole 14. A person skilled in the art will understand that the positioning of the operative suture 20 between the walls of the bone hole and the suture anchor 100 maintains sufficient tension on the operative suture, and the suture anchor bone-engaging features described herein reduce the chances of suture migration. FIG. 9 further illustrates that the reverse angle barbs 109 are arranged such that they engage the operative suture 20 on the tissue load side of the anchor 100 (i.e., the side closest to the repaired soft tissue) as the reverse orientation of the barbs 109 is configured to hold the operative suture at a greater tension relative to the barbs 107.

The methods and systems described herein can have different variations. For example, in each of the embodiments, multiple sutures can be used to couple tissue to bone. Also, one or more operative sutures can be loaded within the anchor before or during a surgical procedure. For example, in some embodiments, a suture anchor can have at least one operative suture pre-loaded thereto such that the suture anchor includes the suture. Furthermore, in some embodiments, the anchor may be pre-loaded on the inserter shaft. In some instances, a tray or other container will contain multiple suture anchors and a single inserter tool can be used to attach to a suture anchor, implant it, connect to another suture anchor, implant it, etc.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device, e.g., the shafts, can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the components of the system described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or highenergy electrons. The radiation kills bacteria on the instrument and in the container. The sterilized instrument can then be stored in the sterile container. The sealed container keeps the instrument sterile until it is opened in the medical facility.

It is preferred the components are sterilized. This can be done by any number of ways known to those skilled in the art including beta or gamma radiation, ethylene oxide, steam, and a liquid bath (e.g., cold soak).

One skilled in the art will appreciate further features and advantages of the described subject matter based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A suture anchor, comprising:
    an elongate body having a proximal end and a distal end and an external surface with a plurality of longitudinally spaced bone-engaging features formed circumferentially thereon over at least a portion of a length of the suture anchor, the proximal end having a lumen extending at least partially into the elongate body and the distal end having a suture engaging feature proximate thereto, wherein the elongate body is unitary,
    wherein a first series of bone-engaging features have a dimension that increases from a distal to a proximal end of each bone-engaging feature of the first series of bone-engaging features, and
    wherein a second series of bone-engaging features have a dimension that decreases from a distal to a proximal end of each bone-engaging feature of the second series of bone-engaging features, wherein the first series of bone-engaging features and the second series of bone-engaging features are formed on the elongate body, form continuous features circumferentially around the elongate body, and mate along two longitudinal lines parallel to the center axis, the center axis extending from the distal end to the proximal end of the elongate body.

2. The suture anchor of claim 1, wherein the second series of bone-engaging features span less than half of a circumference of the elongate body.

3. The suture anchor of claim 2, wherein the second series of bone-engaging features span about 90° to about 120° of the circumference of the elongate body.

4. The suture anchor of claim 1, wherein each bone-engaging feature is a wedge-like barb having a base extending radially from the external surface of the elongate body and a sloped surface extending from the base to the external surface of the elongate body.

5. The suture anchor of claim 4, wherein the first series of bone-engaging features have the base disposed proximal to the sloped surface and wherein the second series of bone-engaging features have the base disposed distal to the sloped surface.

6. The suture anchor of claim 5, wherein the sloped surface is oriented at an angle of about 15° to about 30° relative to a longitudinal axis of the elongate body.

7. The suture anchor of claim 6, wherein the angle is substantially the same for all bone-engaging surface features.

8. The suture anchor of claim 6, wherein the angle is variable based on a longitudinal position of the bone-engaging feature on the elongate body.

9. The suture anchor of claim 8, wherein the angle is greater at a proximal portion of the elongate body than at a distal portion of the elongate body.

10. The suture anchor of claim 1, wherein the lumen extends completely through the elongate body from the proximal end to the distal end.

11. The suture anchor of claim 1, wherein the lumen is offset from the center axis of the elongate body.

12. The suture anchor of claim 1, wherein the suture engaging feature includes an aperture notch in proximity to the distal end.

13. The suture anchor of claim 1, wherein the suture engaging feature includes a pair of longitudinally positioned arms forming a channel arranged proximal to the distal end.

* * * * *